United States Patent
Vietmeier

(10) Patent No.: US 7,243,408 B2
(45) Date of Patent: Jul. 17, 2007

(54) PROCESS METHOD FOR ATTACHING RADIO OPAQUE MARKERS TO SHAPE MEMORY STENT

(75) Inventor: Kristopher Henry Vietmeier, Monticello, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 100 days.

(21) Appl. No.: 10/774,922

(22) Filed: Feb. 9, 2004

(65) Prior Publication Data

US 2005/0172471 A1    Aug. 11, 2005

(51) Int. Cl.
    *B23P 11/02* (2006.01)
(52) U.S. Cl. .................. 29/447; 623/1.34; 148/402; 148/563
(58) Field of Classification Search .......... 29/447; 623/1.13, 1.15, 1.16, 1.18, 1.19, 1.26, 1.34, 623/2.1, 900; 148/563, 402
    See application file for complete search history.

(56) References Cited

U.S. PATENT DOCUMENTS

| | | | |
|---|---|---|---|
| 3,174,851 A | 3/1965 | Buehler et al. | 148/426 |
| 3,351,463 A | 11/1967 | Rozner et al. | 148/426 |
| 3,753,700 A | 8/1973 | Harrison et al. | 148/402 |
| 5,238,004 A | 8/1993 | Sahatjian et al. | 600/585 |
| 5,485,667 A | 1/1996 | Kleshinski | 29/447 |
| 5,725,570 A | 3/1998 | Heath | 623/1.2 |
| 5,725,572 A | 3/1998 | Lam et al. | 623/1.16 |
| 5,741,327 A | 4/1998 | Frantzen | 623/1.34 |
| 5,807,404 A | 9/1998 | Richter | 623/1.16 |
| 5,836,964 A | 11/1998 | Richter et al. | 606/194 |
| 5,858,556 A | 1/1999 | Eckert et al. | 428/586 |
| 5,922,005 A | 7/1999 | Richter et al. | 606/192 |
| 6,022,374 A | 2/2000 | Imran | 623/1 |
| 6,059,810 A | 5/2000 | Brown et al. | 606/198 |
| 6,099,561 A | 8/2000 | Alt | 623/1.44 |
| 6,174,329 B1 | 1/2001 | Callol et al. | 623/1.34 |
| 6,261,319 B1 | 7/2001 | Kveen et al. | 623/1.15 |
| 6,290,721 B1 | 9/2001 | Heath | 623/1.15 |
| 6,293,966 B1 | 9/2001 | Frantzen | 623/1.15 |
| 6,329,069 B1 | 12/2001 | Azizi et al. | 428/600 |
| 6,334,871 B1 | 1/2002 | Dor et al. | 623/1.34 |
| 6,464,720 B2 | 10/2002 | Boatman et al. | 623/1.15 |

(Continued)

FOREIGN PATENT DOCUMENTS

EP    1 356 789 A1    4/2003

(Continued)

OTHER PUBLICATIONS

A Survey of Stent Designs: From Min Invas Ther & Allied Technol 2002: 11(4) 136-147 (© 2002) Pertinent pp. 145-147; D. Stoeckel, C. Bonsignore, and S. Duda.

*Primary Examiner*—Jermie E. Cozart
(74) *Attorney, Agent, or Firm*—Vidas, Arrett, Steinkraus

(57) ABSTRACT

A process comprising the steps of providing a precursor for an implantable medical device, at least a portion of the precursor made of a shape memory material, the shape memory material having a receptacle for receiving a marker therein, the shape memory material having an austenitic and a martensitic phase; enlarging the receptacle while the shape memory material is in the martensitic phase; inserting a marker in the receptacle while the shape memory material is in the martensitic phase; and thereafter transforming the precursor to the austenitic phase.

39 Claims, 5 Drawing Sheets

U.S. PATENT DOCUMENTS

| | | | |
|---|---|---|---|
| 6,464,723 B1 | 10/2002 | Callol | 623/1.34 |
| 6,471,721 B1 | 10/2002 | Dang | 623/1.34 |
| 6,503,271 B2 | 1/2003 | Duerig et al. | 623/1.15 |
| 6,508,803 B1 | 1/2003 | Horikawa et al. | 604/523 |
| 6,527,802 B1 | 3/2003 | Mayer | 623/1.49 |
| 6,540,774 B1 | 4/2003 | Cox | 623/1.15 |
| 6,544,222 B1 | 4/2003 | Yang | 604/103.01 |
| 6,585,757 B1 | 7/2003 | Callol | 623/1.16 |
| 6,620,192 B1 | 9/2003 | Jalisi | 623/1.15 |
| 6,623,520 B2 | 9/2003 | Jalisi | 623/1.15 |
| 6,638,301 B1 | 10/2003 | Chandrasekaran et al. | 623/1.34 |
| 6,669,722 B2 | 12/2003 | Chen et al. | 623/1.15 |
| 6,743,252 B1 | 6/2004 | Bates et al. | 623/1.15 |
| 6,863,685 B2 | 3/2005 | Davila et al. | 623/1.34 |
| 7,037,330 B1 | 5/2006 | Rivelli, Jr. et al. | 623/1.15 |
| 2003/0083736 A1 | 5/2003 | Brown et al. | 623/1.16 |
| 2005/0060025 A1 | 3/2005 | Mackiewicz et al. | 623/1.34 |

FOREIGN PATENT DOCUMENTS

| | | |
|---|---|---|
| EP | 1 488 763 A2 | 3/2004 |

PROCESS METHOD FOR ATTACHING RADIO OPAQUE MARKERS TO SHAPE MEMORY STENT

FIELD OF THE INVENTION

The present invention relates to the attachment of markers to implantable medical devices, in particular a method of attaching radiopaque markers to stents for enhancing the visibility of the device when viewed through a fluoroscope or other imaging device.

BACKGROUND OF THE INVENTION

It is known to implant medical devices such as stents, stent-grafts, vena cava filters, and so forth, into body lumens, such as arteries to reinforce, support, repair or otherwise enhance the blood flow through the lumen.

Stents are commonly used where an artery is blocked, or otherwise damaged. The stent, once in place, reinforces that portion of the artery allowing normal blood flow to occur through the artery. One type of stent that is popularly used for such purposes is a radial expandable stent. This is a tubular or cylindrical stent which can be radially expanded from a first smaller diameter to a second larger diameter. These stents are either self-expanding, or are pressure-expandable.

The stents are inserted into an artery through the use of a stent delivery device and are fed internally through the arterial pathways of the patient until the unexpanded stent is located where desired. The catheter may either be fitted with a balloon in the case of a pressure expandable stent, or with stent retaining sleeves in the case of a self-expanding device. These expandable stents have properties such that they remain expanded after the catheter has been removed.

In the use of radially expandable surgical stents, it is important to precisely determine the position of the stent, both before, during and after it is implanted and expanded. Stents are typically formed of metals or metal alloys including stainless steel, shape memory alloys, such as nickel-titanium alloys, or some other such alloy which in and of themselves are not readily visible using fluoroscopic imaging techniques.

To achieve precise positioning, stents have been paired with image markers to visualize the stent during the time that they are being deployed and also after they have been deployed, at periodic time intervals. Various attempts have been made to attach markers to stents, such that marker is carried by the stent.

Methods of attaching radiopaque material to medical devices through various mechanical and bonding techniques have previously been disclosed. Examples of such methods may be found in U.S. Pat. No. 5,741,327, U.S. Pat. No. 6,022,374, U.S. Pat. No. 6,334,871, U.S. Pat. No. 6,503,271, and U.S. Pat. No. 6,464,720. Prior methods can have various limitations. Among other things, through various prior attaching methods, the resulting stents have burs, weld markings and/or deformation markings on the marker or the stent. Prior methods can also be tedious in the attachment to the stent resulting in decreased efficiency in production, and they can also be difficult to attach in a precise location. There continues to be a need in the art for new and improved radiopaque markers for use on radially expandable stents which can be utilized on stents of all different sizes and provide clear images on a fluoroscope or other medical imaging device. Furthermore, there remains a need in the art for a simple method of fabrication for such radiopaque stents.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed toward a method of attaching markers to medical devices by using the superelastic and/or shape memory properties of shape memory materials. The method involves providing a medical device, such as stent, memory materials. The method involves providing a medical device, such as stent, which is at least partially made of a shape memory material. A receptacle, such as a hole or eyelet, is provided in the shape memory material of the medical device. The marker is to be made of a material which is observable via an imaging device, such as x-ray or MRI devices.

The shape memory material which forms the receptacle has a martensitic phase and an austenitic phase. Such materials are well known in the art. The device is first cooled to, at or below, its martensite start temperature, preferably, at or below the martensite finish temperature. The receptacle is than expanded by placing strain on the shape memory material.

The marker is then placed within the receptacle. The shape memory material is then heated to, at or above, the material's austenite start temperature, preferably, at or above the austenite finish temperature. The marker is thereby engaged and held fast by the shrinking receptacle.

Although stents are the dominantly discussed medical device discussed in the detailed description below, it should be understood that the present inventive method further applies to other medical devices which incorporate markers for purposes of internal positioning and/or monitoring in medical procedures. Such medical device include, but are not limited to, stents, stent-grafts, vena cava filters, and so forth.

Among other things, the present inventive method allows for the attachment of markers onto medical devices using the superelastic properties of shape memory material without the use of certain processes, such as swaging, welding or brazing the marker into a precut hole. Among other things, the present method may allow one to attach markers to medical devices without resulting markings, such as burrs, burns or deformation marks. It also provides the ability to attach brittle or low percentage strain to failure markers, which cannot be swaged or welded, as well as more predictable securement performance.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiment to the invention.

BRIEF DESCRIPTION OF THE SEVERAL VIEWS OF THE DRAWINGS

Referring to the Drawings, wherein like numerals represent like parts throughout the several views.

DETAILED DESCRIPTION OF THE INVENTION

Figure 1:
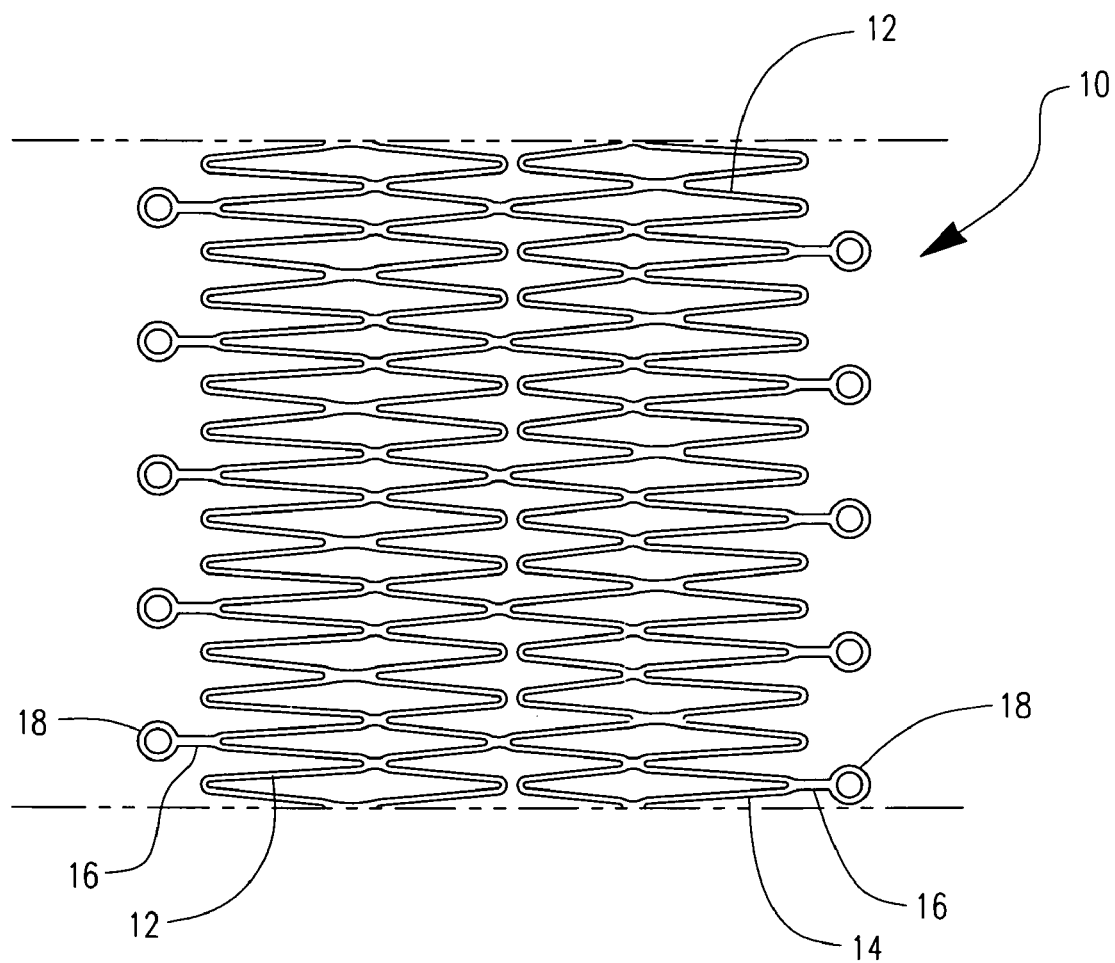
FIG. 1 shows an illustrative stent, which is presented in sheet form.

While this invention may be embodied in many different forms, there are described in detail herein specific embodiments of the invention. This description is an exemplification of the principles of the invention and is not intended to limit the invention to the particular embodiments illustrated. The concepts described above are considered to be read into the further description below.

For the purposes of this disclosure, like reference numerals in the figures shall refer to like features unless otherwise indicated.

As mentioned above, the inventive method will be described predominantly as it applies to stents. This is for illustrative purposes and, as described above, it should be understood that the inventive method may be applied to other implantable medical devices.

The manufacturing and use of stents is well known. Stents, among other ways, may be made by shaping metal wire into desired configurations, linking a plurality of tubular shaped configurations or cutting a particular shape from a sheet of material and subsequently rolling it to form the desired stent. Many stents themselves are made from shape memory material. When this is the case, the receptacle may be formed in a desired location in the body of the stent material. For the purposes of the present invention, when the material used to form the body of the stent is not shape memory material, a receptacle must be secured to the body of the stent material, using suitable bonding techniques.

The receptacle, which eventually holds the marker, may take a variety of forms and shapes and be made of any shape memory or super elastic alloy which is suitable for implantable medical devices. A circular shape is shown in the accompanying illustrations, although the receptacle can have any shape, including shapes with corners and multiple sides. However, the receptacle must merely comprise sufficient inner surfaces so as to, when contracted, adequately constrict around and hold the marker.

Figure 2:
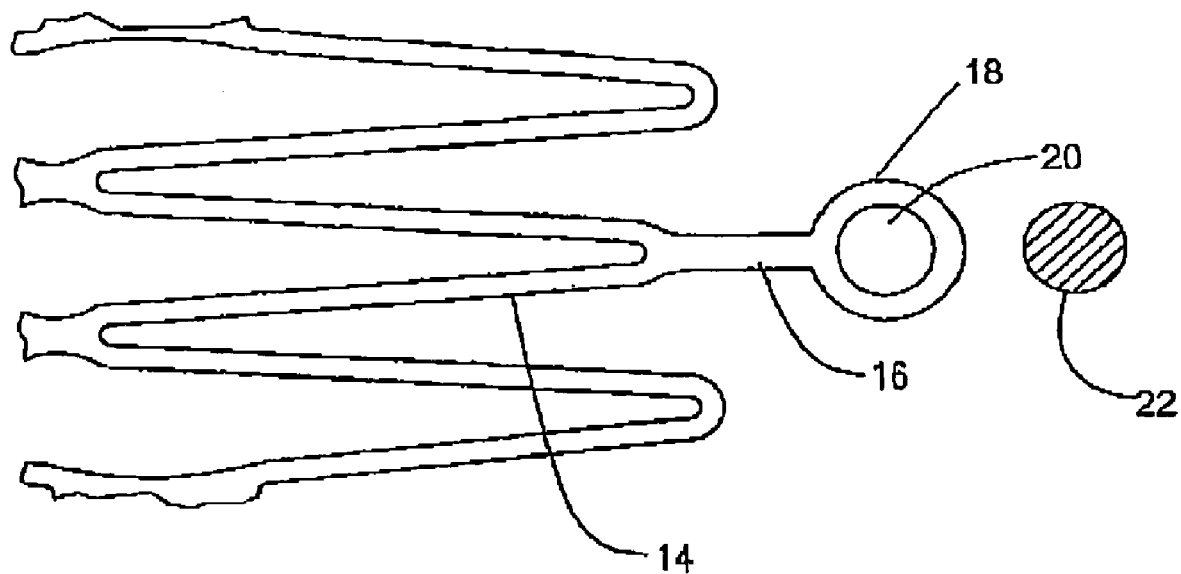
FIG. 2 shows an isolated portion of the stent of FIG. 1.

Referring now to FIG. 1, a stent is generally shown at 10 in the flat form. This particular illustrative stent 10 comprises a plurality of struts 12 joining to form the wall of the stent 10. In this particular embodiment, extending from two joining struts, as shown at 14, is a receptacle support 16. In this particular embodiment, the receptacle support 16 carries the receptacle 18, which, is this case, is circular in shape. A closer view may be seen in FIG. 2.

As mentioned above, the receptacle may be attached to the body of the stent or, as shown here, may be formed from the stent material a part of the overall design. As mentioned above, the receptacle 18 comprises shape memory material.

After the receptacle 18 is formed, it is taken to or below its martensite finish temperature. It should be understood that the formation of the stent body may be completed prior to the addition of the marker(s). Prior to cooling of the receptacle, the receptacle is sized the same or slightly smaller than a marker which is to be inserted.

As mentioned above, the shape memory material which forms the receptacle has a martensitic phase and an austenitic phase. Such materials are well known in the art. Actual martensitic start and finish temperatures are dependent upon material type and process history.

The device, or at least the receptacle, is first cooled to a temperature below the material's martensite start temperature. In one embodiment, the material is cooled to, at or below, its martensite finish temperature. The receptacle is then maintained in its martensitic state below the materials As (Austenite start) temperature.

The inner confines 20 of the receptacle 18 are then enlarged to receive a marker 22. This enlarging may be accomplished via any suitable means. The inner surfaces of the receptacle 18, which define the inner confines 20, are strained to increase the inner confines 20 to a point which is adequate to receive the marker 22. This may be done, among other ways, by inserting a tapered mandrel to expand the hole. The tapered mandrel may optionally be placed in an expandable hypo tube, the hypo tube having been placed in the hole. The hypo tube is used so as to not damage the hole with the insertion of the mandrel.

The hole is increased in size dependent upon the size of the marker. The strain imparted to the hole should not exceed that which would impart permanent deformation of the material. Strain application and dimension guidelines are dependent upon the specific material type being used.

In one example, using a Nitinol stent, the hole is increased in size by applying 8-10% strain. A hole about 0.025 inches in diameter would be increased by about 0.0025 inches, i.e. about 10%. The hole should be sized so as to allow the marker to have a zero force fit. For the above hole of about 0.025 inches, this would be about 0.0025 inches in clearance in the receptacle's cold state.

Figure 3:
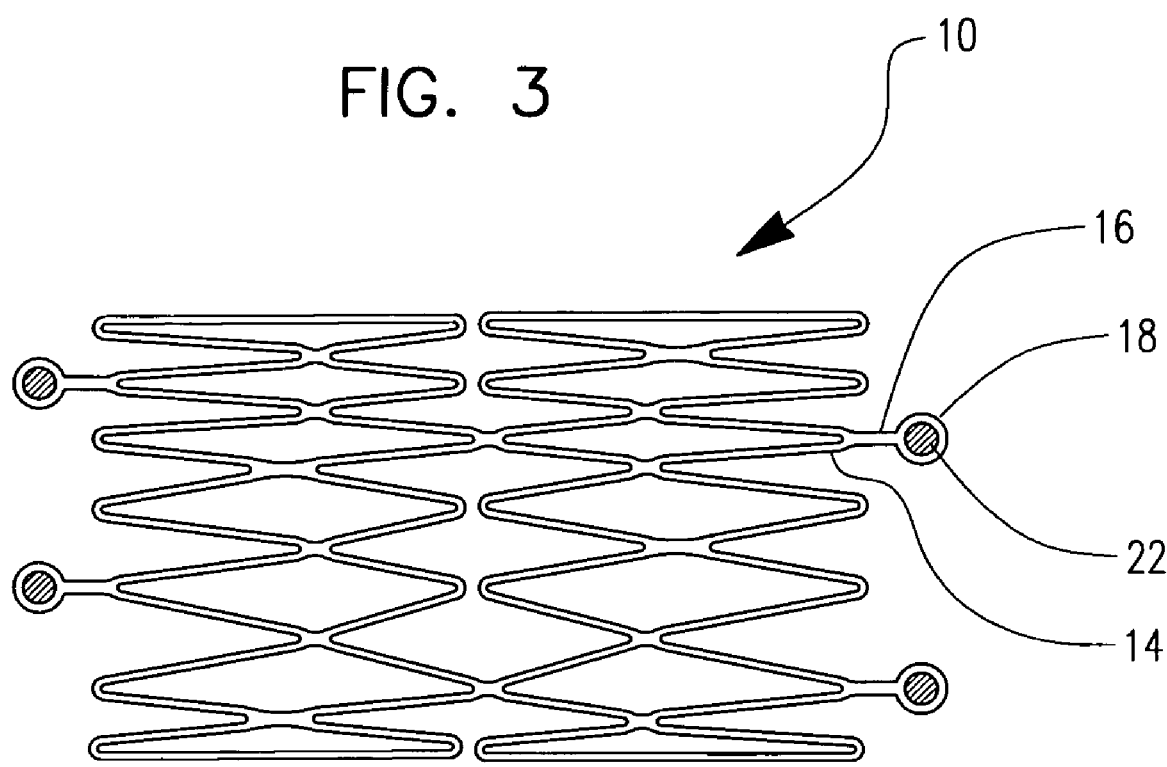
FIG. 3 shows an illustrative stent having inserted markers.

The marker 22 is then placed within the inner confines 20 of the receptacle 18. The receptacle 18 is then heated to or above its austenite finish temperature. As this heating occurs, the inner confines 20 of the receptacle 18 are reduced and the inner surfaces of the receptacle 18 engage and grip the marker 22, as shown in FIG. 3.

After the marker is inserted, it may be locally heated prior to heating the entire stent to cause the opening to close in around it. This allows multiple markers to be placed prior to heating the entire stent. The shape memory material is then heated to a point at, or above, the material's austenite start temperature, preferably, at or above the material's austenite finish temperature. The marker is thereby engaged and held fast by the shrinking receptacle.

Another variation of the above method would be to strain the material first, and then cool the material to a temperature, at or below the Ms temperature, as discussed above. In this variation, the martensitic phase would be stress induced and thereafter the temperature would be maintained.

Figure 4:
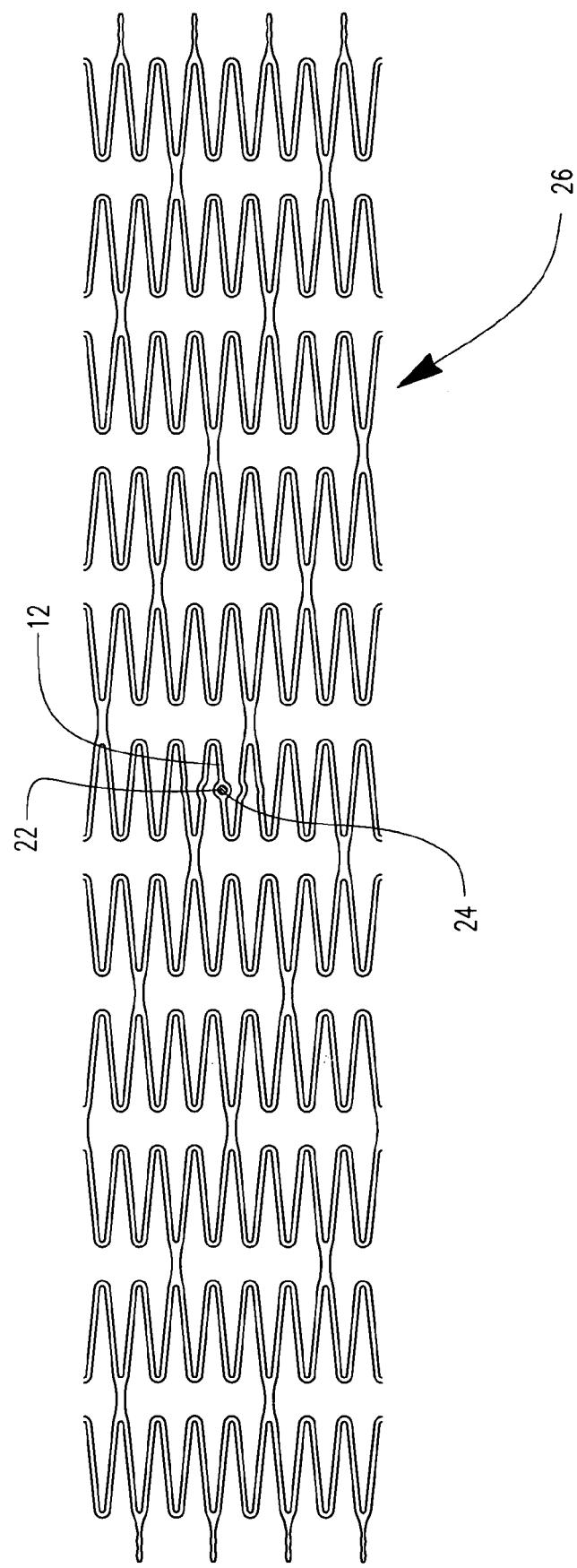
FIG. 4 shows an illustrative stent, which is presented in sheet form.
Figure 5:
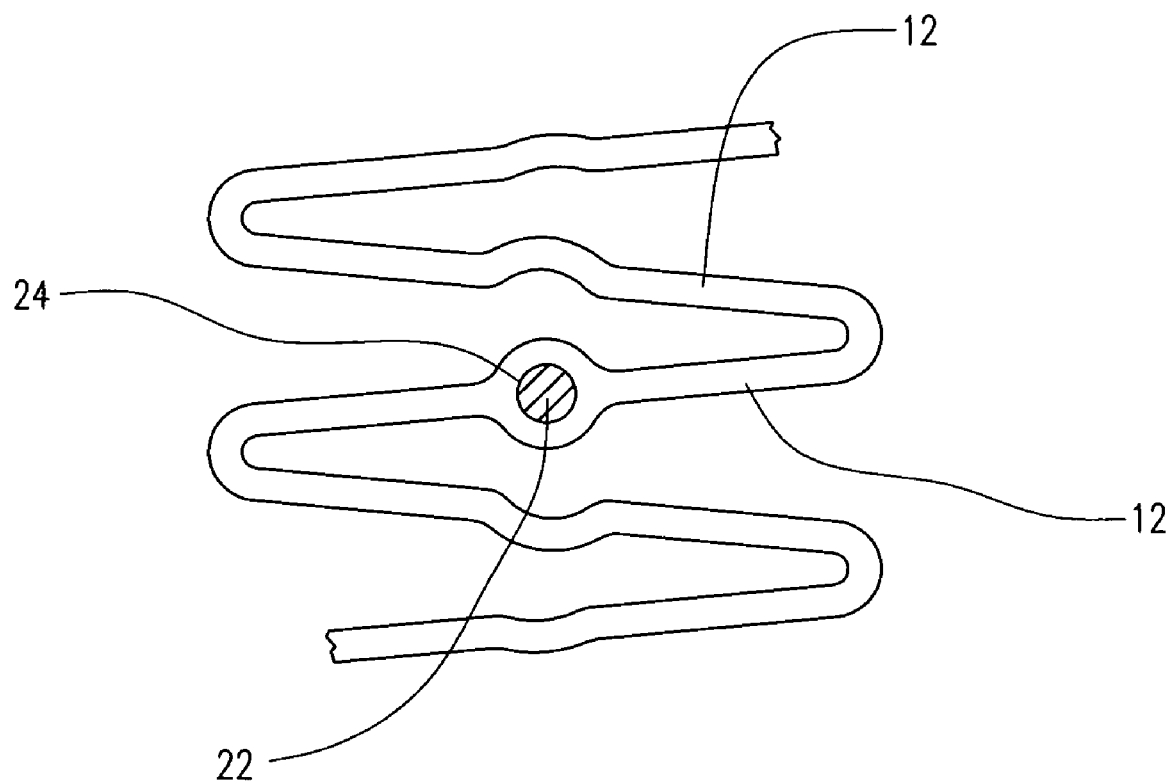
FIG. 5 shows an isolated portion of the stent of FIG. 4.

FIG. 4 illustrates a further possible positioning of a marker in a stent. As can be seen, the receptacle 24 is positioned at the interior of the stent 26 body. The receptacle 24, in this particular embodiment, is formed within one of the stent's 26 struts 12. As mentioned above, the receptacle 26 may be a separate shape memory piece or it may be part of the stent material if the material which makes up the stent is shape memory material. FIG. 5 shows a blown up portion of the stent 26, illustrating the marker's 22 placement within the receptacle 24.

Markers are well known in the present field of art. Markers are used to improve opacity under fluoroscopy. For stents, such as Nitinol stents, which do not exhibit the preferred amount of opacity, radiopaque markers are connected to the stent using the inventive method described herein. Suitable types of markers are determined by the imaging device being used to identify the marker within the body. Radiopaque markers are most commonly used in the placement of stents. They include, but are not limited to, tantalum, gold, iridium and platinum. MRI sensitive materials may also be used when MRI is used to identify the positioning of the marker. Similarly, ultrasonic markers may be added when ultrasound is used.

As mentioned above, the marker may be added to a finished stent or prior to polishing.

As mentioned above, the present inventive method may apply to the attachment of markers to other implantable medical devices, such as, but not limited to stent-grafts, distal protection filters, embolic coils, grafts, and vena cava filters. Also, the methods disclosed herein may be utilized with catheters and guidewires. Following the method described herein, a receptacle may be formed as part of the medical devices and manipulated using the properties of shape memory materials to receive and constrict around a chosen marker.

It should also be understood that other items, other than markers, may be attached to medical devices using the inventive method. Such item include, but are not limited to, sensors, batteries, sleeves or coverings, cavities or cups for containing drugs, filters, wires, tubes and processing chips.

The present inventive method allows the attachment of materials that are rigid, that cannot be swaged or that are not plastically deformable without leaving deformation marks as the result of insertion. As such, the present inventive techniques may be used in joining other materials, such as guidewires to other elements of a catheter, wires of different materials, such nitinol wires to non-nitinol wires, and catheter tubes made of different materials.

The present invention is also directed to stents having shape memory receptacles with markers being positioned therein. The present invention is also directed toward medical devices manufactured using any of the inventive techniques disclosed herein.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A process comprising the steps of:
   a) providing a precursor for an implantable medical device, at least a portion of the precursor made of a shape memory material, the shape memory material having a receptacle for receiving a marker therein, the shape memory material having an austenitic and a martensitic phase, the receptacle having a first shape when there is no marker therein and the shape memory material is in the martensitic phase;
   b) enlarging the receptacle while the shape memory material is in the martensitic phase;
   c) subsequently inserting a marker in the receptacle while the shape memory material is in the martensitic phase, the receptacle having a second shape after the marker is inserted into the receptacle, the second shape the same as the first shape; and thereafter
   d) transforming the precursor to the austenitic phase.

2. The process of claim 1, wherein the precursor is a stent precursor.

3. The process of claim 1, wherein the precursor is chosen from the group consisting of a stent-graft precursor, a distal protection filter precursor, an embolic coil precursor, a graft precursor, and a vena cava filter precursor.

4. The process of claim 1, the precursor having a plurality of receptacles for receiving a plurality of markers.

5. The process of claim 4, wherein heat is applied to the plurality of receptacles prior to transforming the precursor to the austenitic phase.

6. The process of claim 1, further comprising the step of post-processing the precursor to form an implantable device suitable for implantation in the body.

7. The process of claim 6, wherein the post-processing includes the step of polishing the precursor.

8. The process of claim 6, where the implantable device is a stent.

9. The process of claim 6, wherein the implantable device is chosen from the group consisting of a stent-graft, a distal protection filter, an embolic coil, a graft, and a vena cava filter.

10. The process of claim 1, wherein the shape memory material is nitinol.

11. The process of claim 1, wherein the shape memory material is polymeric.

12. The process of claim 1, wherein the implantable medical device is a stent, the stent having a first end and a second end, the receptacle being positioned at the first end of the stent.

13. The process of claim 1, wherein the implantable medical device is a stent, the stent having a first end and a second end, the receptacle being positioned between the first end of the stent and the second end of the stent.

14. The process of claim 1, wherein the implantable medical device is formed prior to the receptacle being enlarged.

15. The process of claim 1, wherein the implantable medical device and the receptacle are made from different materials.

16. The process of claim 1, wherein the marker is radiopaque.

17. The process of claim 1, wherein the marker does not comprise material in common with the shape memory material of the implantable medical device and wherein the marker is in direct contact with the shape memory material of the implantable medical device after the precursor is transformed to the austenitic phase.

18. The process of claim 1, wherein the first and second shapes of the receptacle are substantially circular.

19. A process comprising the steps of:
   a) providing a precursor for an implantable medical device, at least a portion of the device made of a shape memory material, the shape memory material having a receptacle for receiving a marker therein, the shape memory material having at least a first phase and a second phase, the receptacle having a first shape in the first phase, the receptacle having a second shape in the second phase, the first shape the same as the second shape;
   b) causing the shape memory material to transition from the first phase to the second phase;
   c) enlarging the receptacle while the shape memory material is in the second phase;
   d) subsequently inserting a marker in the receptacle while the shape memory material is in the second phase; and thereafter
   e) transforming the precursor to the first phase.

20. The process of claim 19, wherein the shape memory material is a metal.

21. The process of claim 19, wherein the metal is nitinol and the first phase is an austenitic phase and the second phase is a martensitic phase.

22. The process of claim 19, wherein the shape memory material is polymeric.

23. The process of claim 19, wherein the precursor is a stent precursor.

24. The process of claim 19, wherein the precursor is chosen from the group consisting of a stent-graft precursor, a distal protection filter precursor, an embolic coil precursor, a graft precursor, and a vena cava filter precursor.

25. The process of claim 24, wherein heat is applied to the plurality of receptacles prior to transforming the precursor to the austenitic phase.

26. The process of claim 23, wherein the shape memory material is polymeric.

27. The process of claim 23, the precursor having a plurality of receptacles for receiving a plurality of markers.

28. The process of claim 19, further comprising the step of post-processing the precursor to form an implantable device suitable for implantation in the body.

29. The process of claim 28, wherein the post-processing includes the step of polishing the precursor.

30. The process of claim 28, where the implantable device is a stent.

31. The process of claim 28, wherein the implantable device is chosen from the group consisting of a stent-graft, a distal protection filter, an embolic coil, a graft, and a vena cava filter.

32. The process of claim 19, wherein the shape memory material is nitinol.

33. The process of claim 19, wherein the implantable medical device is a stent, the stent having a first end and a second end, the receptacle being positioned at the first end of the stent.

34. The process of claim 19, wherein the implantable medical device is a stent, the stent having a first end and a second end, the receptacle being positioned between the first end of the stent and the second end of the stent.

35. The process of claim 19, wherein the implantable medical device is formed prior to the receptacle being enlarged.

36. The process of claim 19, wherein the implantable medical device and the receptacle are made from different materials.

37. The process of claim 19, wherein the marker is radiopaque.

38. The process of claim 37, wherein the marker does not comprise material in common with the shape memory material of the implantable medical device and wherein the marker is in direct contact with the shape memory material of the implantable medical device after the precursor is transformed to the first phase.

39. The process of claim 19, wherein the first and second shapes of the receptacle are substantially circular.

* * * * *